United States Patent [19]

Mills et al.

[11] Patent Number: 5,398,700
[45] Date of Patent: Mar. 21, 1995

[54] SURGICAL DRAPE WITH IMPROVED CONSTRUCTION FOR CRITICAL ZONE PANEL

[75] Inventors: Veronica A. Mills, Cincinnati; Jeffrey L. Taylor, Wyoming, both of Ohio

[73] Assignee: Standard Textile Company, Inc., Cincinnati, Ohio

[21] Appl. No.: 84,001

[22] Filed: Jun. 29, 1993

Related U.S. Application Data

[63] Continuation-in-part of Ser. No. 680,089, Apr. 3, 1991, Pat. No. 5,222,507.

[51] Int. Cl.[6] .............................................. A61B 19/00
[52] U.S. Cl. ...................................... 128/853; 128/849
[58] Field of Search ................ 128/849, 850, 851, 852, 128/853, 854, 855, 856, 846

[56] References Cited

U.S. PATENT DOCUMENTS

| | | | |
|---|---|---|---|
| 3,669,106 | 6/1972 | Schrading et al. | 128/853 |
| 3,721,234 | 3/1973 | Hadtke et al. | 128/852 |
| 4,040,418 | 8/1977 | Collins | 128/852 |
| 4,089,331 | 5/1978 | Hartigan et al. | 128/853 X |
| 4,134,398 | 1/1979 | Scrivens | 128/852 |
| 4,275,720 | 6/1981 | Wichman | 128/853 |
| 4,323,062 | 4/1982 | Canty | 128/852 |
| 4,957,120 | 9/1990 | Grier-Idris | 128/853 X |
| 5,002,070 | 3/1991 | Taylor | 128/853 |
| 5,038,798 | 8/1991 | Dowdy et al. | 128/849 X |

Primary Examiner—Sam Rimell
Attorney, Agent, or Firm—Kinney & Schenk

[57] ABSTRACT

A surgical drive comprises a main panel and a "critical zone" panel secured thereto. A fenestration is formed by cutting through the "critical zone" panel. The main panel is a light weight fabric having a relatively high coefficient of friction. The "critical zone" panel comprises a barrier panel lying against the main panel and an outwardly facing absorbent panel, having an irregular surface. The critical "critical zone" panel is folded to form troughs for capturing liquid incident to a surgical procedure. Corner constructions close the ends of the troughs.

12 Claims, 4 Drawing Sheets

SURGICAL DRAPE WITH IMPROVED CONSTRUCTION FOR CRITICAL ZONE PANEL

The present invention is a continuation in part application of the prior application of one of the applicants in the present invention, said prior application being identified as Ser. No. 680,089, filed Apr. 3, 1991, U.S. Pat. No. 5, 222, 507 which application is of common assignment with the present application.

The present invention relates to improvement in surgical drapes.

In the performance of surgical procedures, it is a customary and usual practice to limit the extent to which body liquids, or fluids used in the procedure, will come into contact with the skin surfaces of the patient. One of the reasons for this practice is based on the theory that micro-organisms migrate through a liquid medium instantaneously. Therefore, if there are any micro-organisms on the skin surface of the patent, a surgical drape inhibits their transfer to the surgical site.

To limit the spread of micro-organisms, clothes are draped over the patient so that only the area immediately adjacent to the area of the surgical site is exposed. The clothes, or surgical drapes, as they are generally designated, limit contact between the skin surface and blood, or other body liquid, which might exude from an incision. Surgical drapes also limit the extent to which liquids, employed in a procedure, contact the skin surface of a patient.

The use of surgical drapes is more than a matter of general cleanliness and comfort, since microorganisms on the skin of the patient can be the source of infection.

The present invention is, more specifically, directed to improvements in fenestrated, surgical drapes. This type of is provided with a fenestration, usually within the outline of the drape, though sometimes opening from a side of the drape. The fenestration is registered with the site of the surgical procedure. The area and shape of the fenestration is such as to minimize the area of the patient's skin that is exposed by the fenestra, consistent with the nature of the procedure to be performed. There are a wide variety of fenestrated, surgical drapes, which are specifically designed for use in the performance of various surgical procedures.

As indicated, the general purpose of a surgical drape is to minimize the area of a patient's person that is directly exposed to contact with liquids, including body fluids, that are incident to the performance of a surgical procedure. In some cases there can be substantial quantities of body fluids that emanate from the surgical site. The area marginally of a fenestration (i.e., immediately adjacent and withing a foot or so of the fenestration) is referenced as a "critical zone" due to the large amount of body fluids and other liquids that can be found in this region. To guard against such liquids penetrating (striking through) the drape and possibly contaminating the underlying portion of the patient's person, it has been an accepted practice to provide a "critical zone" panel, which overlays the main panel of the drape and provides additional barrier protection for preventing such liquids from striking through to the patient's person.

During the performance of a surgical procedure, the amount of body liquids and other liquids incident to the performance of the procedure can be so great that they spill, from the area or the fenestration and the "critical zone" panel, and fall onto the operating room floor. Such spillage creates a hazard in that possibly infectious microorganisms are spread from the surgical site, making their containment more difficult. Further, the liquids could cause a doctor or operating room assistant to slip and fall. This could cause injury to the person falling, as well as jeopardizing the well being of the patient.

It is also to be noted that it is an accepted practice to place surgical instruments on the drape protected patient during the performance of a surgical procedure. This practice can, at times, result in the instruments slipping from the drape and falling to the operating room floor. Not only can this cause damage to the instrument, also, as is the case, with spilled liquids, the fallen instrument increases the area of contamination and increases the likelihood of a slip and fall accident.

At this point, it will be further noted that there are two primary classifications of surgical drapes, one being disposable and the other being reusable.

Disposable surgical drapes are generally formed of non-woven fibers and, as the name implies, are simply discarded after a single use. Disposable drapes are relatively inexpensive, but their disposal has become a problem of progressively increasing seriousness, as their potential for pollution of the environment becomes better recognized.

Reusable surgical drapes, as that name also implies, are laundered and sterilized after each use, so that they may be employed several times. Reusable surgical drapes are, generally, constructed of woven or knit fabrics, which have a "hand", or tactile handling characteristic that facilitates their use and is preferred by medical professionals. The acquisition cost of reusable surgical drapes is higher than that of their disposable counterparts. However, including the costs of washing and sterilization, the per use cost of reusable surgical drapes can be substantially less than that of functionally equivalent disposable drapes.

Accordingly, one object of the present invention is to minimize, if not eliminate the spilling of body liquids and other liquids incident to the performance of a surgical procedure, from spilling from a surgical drape and onto the operating room floor.

A related end sought by the foregoing object is to decrease the exposure of operating room personnel to possibly infections liquids by physically containing such liquids so that they will not spill to the floor and splatter, or other wise become airborne, or so spread that the exposure to infectious microorganisms is increased.

A related object of the present invention is to minimize the possibility of instruments falling from a surgical drape and onto the operating room floor, during the performance of a surgical procedure.

A more specific object of the present invention is to prevent spillage of liquids from troughs formed on the side edges of the "critical zone" panel of a surgical drape.

Another object of the present invention is attain the foregoing end by means of a trough corner construction which is releasably secured to facilitate thorough washing of the surgical drape.

Yet another object of the present invention is to provide a surgical drape that attains the foregoing ends and is, additionally, to achieve these ends by a simplified construction that has the necessary ruggedness for multiple uses and multiple laundering/sterilization cycles.

In accordance with one aspect of the invention, the foregoing objects may be attained by a reusable, surgical drape adapted to overlie a patent during the performance of a surgical procedure and having a fenestration for registration with the site of a surgical procedure. The drape comprises a main panel of a given lateral extent, and has side portions adapted to drape beneath the level of an operating table on which a patient is positioned.

A "critical zone" panel of substantially smaller lateral extent extends outwardly from the fenestration. The "critical zone" panel is generally rectangular and has side portions generally parallel with the side portions of the main panel. The "critical zone" panel extends outwardly on opposite sides of the fenestration to a point where the "critical zone" panel and the main panel are both angled from a horizontal plane, when the surgical drape is draped over a patient.

Further the "critical zone" panel comprises a barrier panel and is characterized in that the marginal edge portions of the barrier panel, on opposite sides thereof, are folded on themselves to define troughs having bottom, folded portions. The marginal side edges are in spaced relation to the main portion of the barrier panel and form upwardly open, non-filled troughs of substantial depth, extending upwardly from the bottom folded portions, for the reception therein of liquids incident to the performance of a surgical procedure, as well as to trap surgical instruments, or the like which might slip from a position on the "critical zone" panel adjacent the fenestration.

The drape is further characterized by means for releasably securing said marginal edge portions of the barrier panel to the main portion of the barrier panel, whereby the surgical drape may be washed and sterilized with the barrier panel in an unfolded condition.

Further advantage is found where the "critical zone" panel overlies the main panel and the fenestration opening is defined by both the main panel and the "critical zone" panel. The fenestration is further defined by a tape edge binding that secures the "critical zone" panel to the main panel. Additionally the "critical zone" panel is further secured to the main panel by stitchings that extend marginally of the ends of the "critical zone" panel, and terminate adjacent the edges of the folded marginal, trough forming portions of the "critical zone" panel.

In accordance with other aspects of the invention the above stated objects may be attained by a reusable, surgical drape adapted to overlie a patent during the performance of a surgical procedure and having a fenestration for registration with the site of a surgical procedure. The drape comprises a main panel of a given lateral extent. A "critical zone" panel of substantially smaller lateral extent and extends outwardly from the fenestration.

The "Critical zone" panel comprises a liquid repellant, barrier panel. A marginal edge portion of the barrier panel is folded on itself to define a bottom, folded portion. The marginal edge portion is in spaced relation to the main portion of the barrier panel and forms an upwardly open, non-filled trough of substantial dept, extending upwardly from the bottom folded portion, for the reception therein of liquids incident to the performance of a surgical procedure, as well as to trap surgical instruments, or the like which might slip from a position on the "critical zone" panel adjacent the fenestration. Means are provided for spacing, the edge of the said marginal edge portions from the main portion of the barrier panel, to define a spaced opening for said non-filled trough.

The drape is characterized by means for releasably securing said marginal edge portion of the barrier panel to the main portion of the barrier panel, and further characterized by means which close the ends of the trough.

It is preferred that the means that close the ends of the trough are releasable to facilitate washing and sterilization of the surgical drape and particularly, the "critical zone" panel thereof.

More specifically it is preferred that the means that close the ends of the trough comprise means for releasably holding portions of the trough forming portions of the "critical zone" panel in further folded relation.

Advantageously, the referenced trough and end closure construction may be formed on opposite sides of the critical zone panel.

Additionally, each releasable fastening means may comprise cooperating male and female snap fasteners. A first set of snap fasteners are disposed along the length of the marginal edge portion of the "critical zone" panel and a second set of snap fasteners are disposed in parallel relation to said marginal edge and inwardly therefrom. The two sets of fasteners are generally aligned in a direction at right angles to said marginal edge, whereby the two sets of fasteners may be engaged to releasably maintain the marginal edge portion of the "critical zone" panel in folded, trough-forming relation about a bottom line.

The releasable means, holding the further folded portions in folded relation closing the ends of the trough, comprise snap fasteners. Additionally, at each corner, the last mentioned snap fasteners may comprise a first male and a first female snap fastener, facing upwardly in the unfolded condition of the "critical zone" panel and a second male and a second female snap fastener, facing downwardly. The first male and first female fasteners are engageable to hold the marginal edge portion corner in folded relation on the main portion of the "critical zone" panel. The second male and second female fasteners are positioned to face upwardly, when the first male and first female fasteners are engaged. The second male and second female fasteners are engageable to hold the folded corner portions of the "critical zone" panel in further folded relation in which the end of the trough is closed.

The above and other objects and features of the present invention will be apparent from a reading of the following description of a preferred embodiment, with reference to the accompanying drawings and the novelty thereof pointed out in the appended claims.

Figure 1:
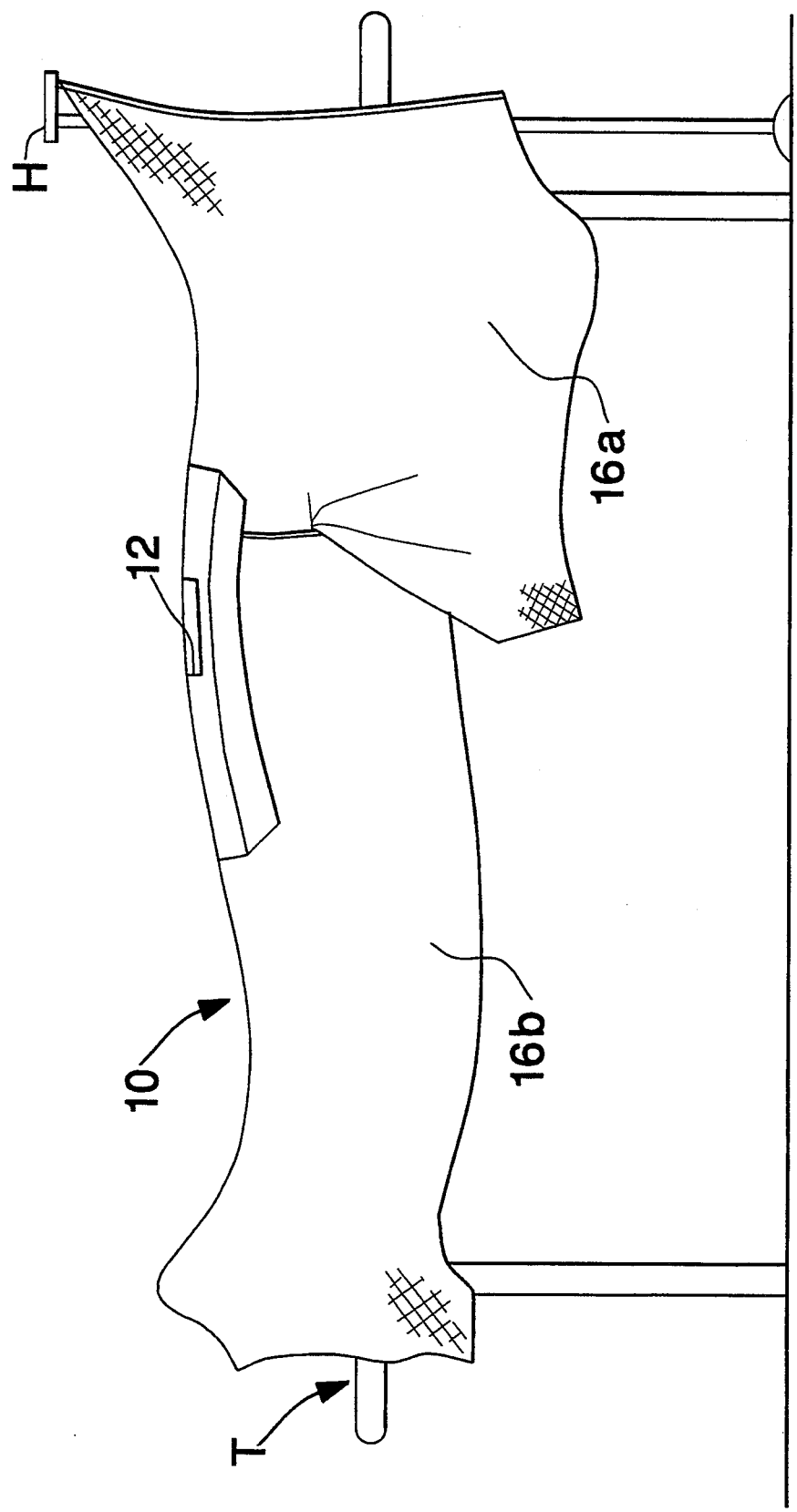
FIG. 1 illustrates the present surgical drape as it would be typically disposed on a surgical patient who is supported on an operating table.

Reference is first made to FIG. 1, which illustrates the present surgical drape, indicated generally by reference character 10, deployed upon a surgical patient, who is lying on his back on an operating table T. The drape 10 is held in spaced relation above the head of the patient by a holder H to provide access to the patient's head by the anesthesiologist.

The drape 10 includes a fenestration (opening) 12, which is registered with the site of the surgical procedure. As illustrated in FIG. 1, this would be in the area of the patient's abdomen. The fenestration 12 is within the confines of a "critical zone" panel 14, which, in turn, is disposed generally centrally of the main panel 16 of the drape 10.

Figure 2:
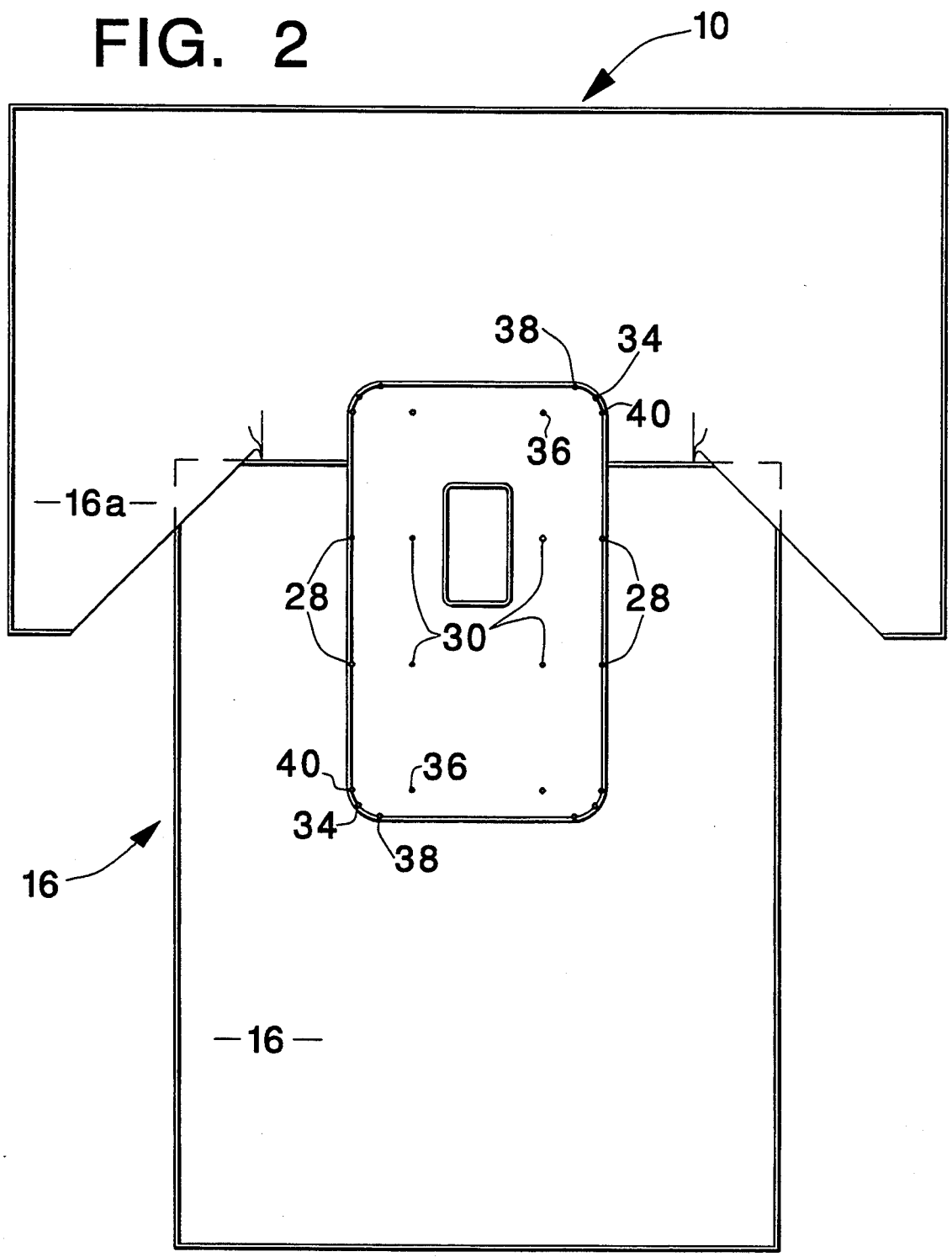
FIG. 2 is a plan view of the drape seen in FIG. 1, with the trough-forming flaps in an unsnapped, flat condition.

Reference is next made to FIG. 2, which better illustrates that the main panel 16, of the drape 10, is compositely formed by panels 16a and 16b, which are appropriately sewed together in a T-shaped configuration. The outline of the main panel 16 is edge bound by a binding tape, in conventional fashion. The panels 16a, 16b are preferably formed of a drapable fabric having a relatively high coefficient of friction, as is taught in U.S. patent application Ser. No. 860,315, filed Mar. 30, 1992, rights in said application also being assigned to the same assignee as the present application. This fabric maintains its desired characteristic through a sufficient number of washing and sterilization cycles for the drape 10 to be relatively inexpensive on a per-use basis.

Figure 3:
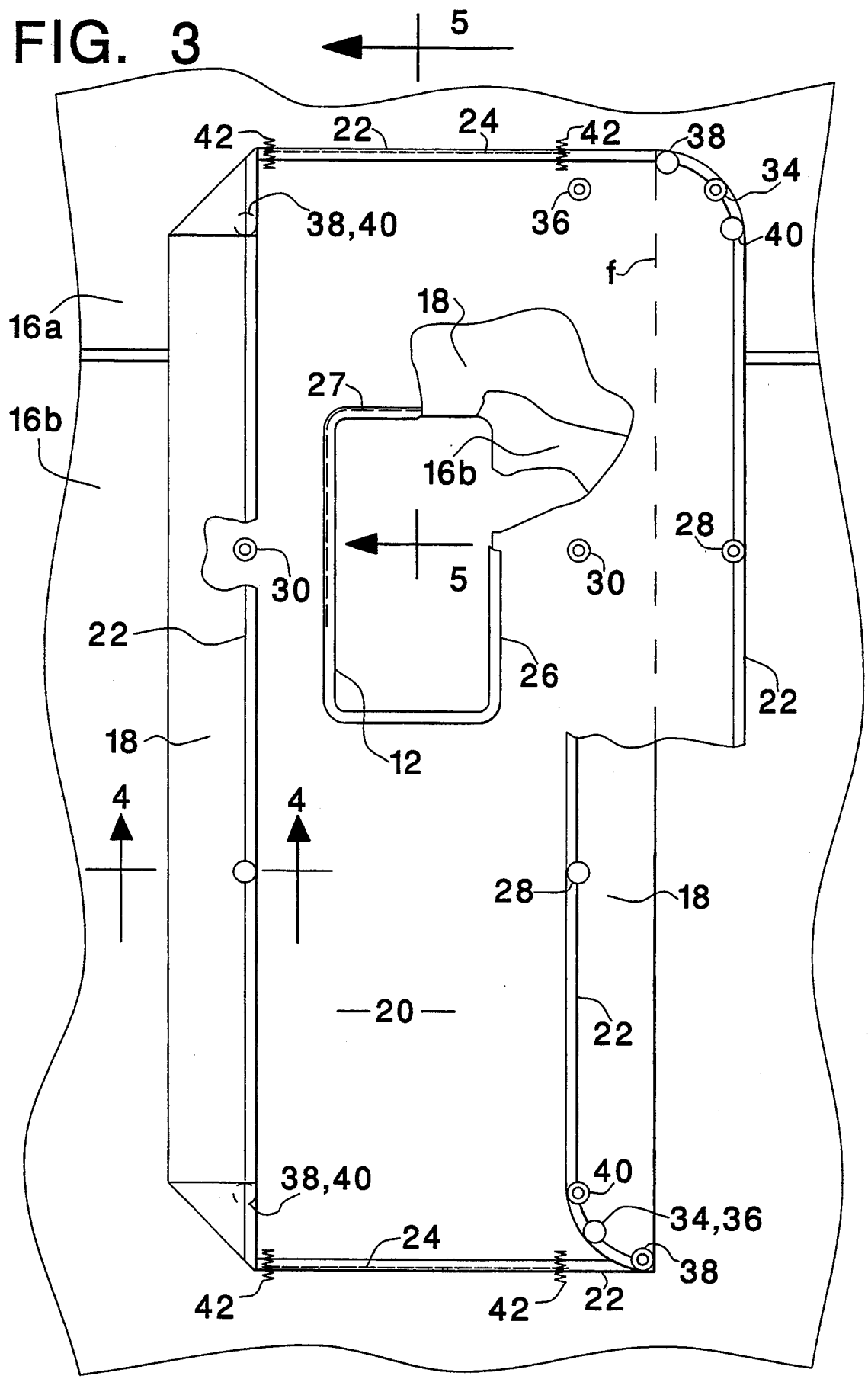
FIG. 3 is a plan view, on an enlarged scale of the "critical zone" panel of the present surgical drape, with the flap on one side of the panel being secured in a trough forming position and with the flap on the other side of the panel being partially secured in a trough forming position.
Figure 4:
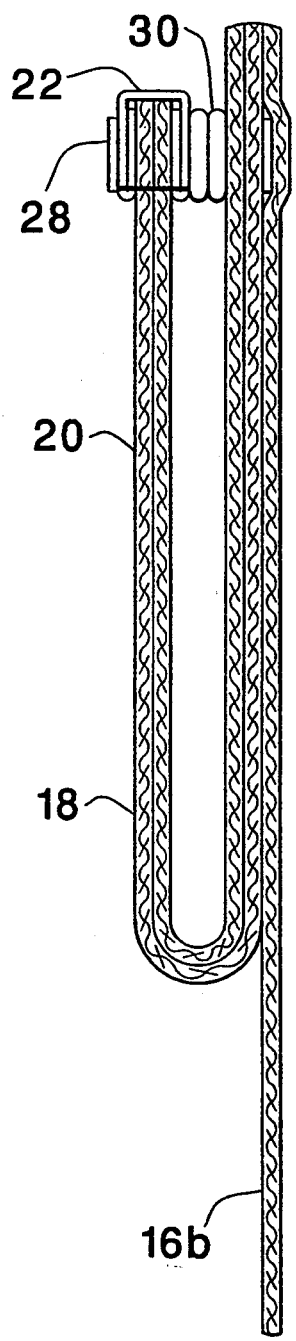
FIG. 4 is a section, on an enlarged scale, taken on line 4—4 in FIG. 3 and oriented to illustrate the relative position of the "critical zone" panel, when the drape is deployed as in FIG. 1.
Figure 5:
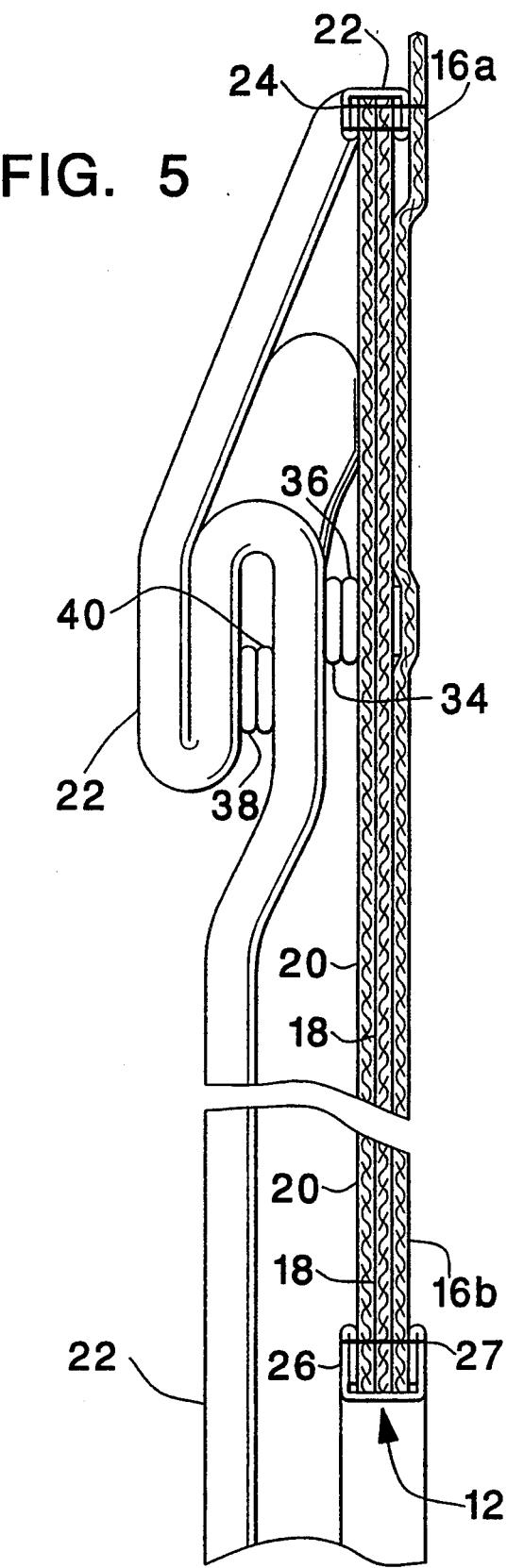
FIG. 5 is a section, on an enlarged scale, taken on line 5—5 in FIG. 3 and oriented as in FIG. 4.

The construction of the "critical zone" panel 14 is best illustrated and understood from FIGS. 3–5. The "critical zone" panel 14 preferably comprises a washable barrier fabric panel 18 that preserves its barrier characteristics through a substantial number of washing/sterilization cycles so that the drape is relatively inexpensive on a per use basis. The barrier fabric may be a woven polyester fabric, which has Suter ratings in excess of 35 after 75 washing/sterilization cycles, as taught in U.S. Pat. No. 4,822,667, rights in which are also assigned to the assignee of the present application. Alternatively the panel 18 may be formed of a "liquid proof" washable fabric A suitable fabric is described in U.S. Pat. 5,183,702.

The upper, or outer, surface of the "critical zone" panel 14 is formed by a panel 20 of absorbent, textured fabric having a relatively high coefficient of friction.

The fabrics designated for the main panels 16a, 16b, and the "critical zone" panels 18 and 20 are, preferably, light weight and drapable, with a relatively high coefficient of friction so that they will not inadvertently slip relative to the person of the patient. A suitable fabric is disclosed in U.S. application Ser. No. 860,315, filed Mar. 30, 1992.

Further teachings regarding the fabrics employed in constructing the present surgical drape are found in the above referenced, parent application Ser. No. 680,089, and are incorporated herein by reference, as if fully rewritten.

The "critical zone" panels 18, 20 are initially secured together by a binding tape 22 that is stitched around the matching peripheries thereof to form a subassembly. After the main panel portions 16a, 16b have been joined to compositely form the main panel 16, the "critical zone" panel, sub-assembly, may be joined to the underlying main panel by stitching 24. The fenestration 12 may then be cut in the fabric layers 20, 18, 16a and 16b. After the fenestration is formed, the edges of the several fabric layers, that define the fenestration, are bound by a binding tape 26, by stitching 27, that extends therethrough.

A series of male snap fasteners 28 are mounted along the marginal side edges of the "critical zone" panel 14. The fasteners 28 are engageable with corresponding female snap fasteners 30 mounted on the "critical zone" pane 14, inwardly of its side edges. When the snap fasteners 28, 30 are engaged, an upwardly open trough 32 is formed along each of the side edges of the "critical zone" panel 14, as is best illustrated in FIG. 4.

In accordance with the present invention, a set of four snap fasteners is provided at each end of the two troughs 32 to form closed corners therefor. It will also be noted that, preferably, the corners of the "critical zone" panel are rounded on a radius that approximates the depth of the trough 32 (note the flap fold line f indicated by broken lines in FIG. 3). The corner forming snaps comprise (in the flat condition of the "critical zone" panel) an upwardly face male snap 34 and an upwardly facing female snap 36 and downwardly facing male snap 38 and female snap 40. In FIG. 3 male fasteners are represented by a solid center and female fasteners are indicated by a central circle.

In forming the trough corners, the "critical zone" panel is folded about the fold line f and the snaps 34 and 36 are engaged, as indicated in the lower right portion of the "critical zone" panel, as illustrated in FIG. 3. The corner is then completed by folding the corner portion of the double thickness of "critical zone" panel on itself to engage the snaps 38, 40, as illustrated in FIG. 5.

The trough corners, thus formed, provide barriers at opposite ends of the troughs 32. The rounded corners of the "critical zone" panel minimize the bulk of fabric at the corners of the troughs 32, where the end closures have been formed.

Thus, during a surgical procedure, substantial quantities of liquid can collect in the troughs 32, without danger of their spilling onto the operating room floor and creating a hazard. In the usual case, liquids are suctioned, sponged or mopped from the trough to obviate the possibility of spilling liquids when the drape is removed from the patient. In any event, with the closed corner construction of the present invention, the danger of liquids inadvertently spilling from the trough is greatly minimized, if not completely eliminated. In any event suctioning of liquid from the trough does not require constant attention, to the end that the surgical assistant, who would perform such task, is available for the performance of other duties.

This corner construction is of further significance in that it facilitates washing of the surgical drape. Thus, after being used, it is a simple matter to release the side forming snaps 28, 30 and the corner forming snaps 34, 36 and 38, 40. The critical zone panel is thus free of any corners or crevices that would impede its being thoroughly cleaned of foreign matter in a washing process employing conventional practices.

It is to be appreciated that the construction of the surgical drape 10 is such as to withstand the considerable abuse incident to the washing and sterilization procedures, as well as what is encountered in use. Thus, the "critical zone" panel is secured to the underlying main panel 16 by the stitchings 24, which extend through the binding tape 22 and by stitching 27, through the binding tape 26, at the fenestration 12. The stitchings 24 terminate, approximately, at the upper end of the troughs 32. Bar tacks 42, extending through the "critical zone" panel and main panel 16, are provided at opposite ends of the stitchings 24.

The snap fasteners herein referenced are of a well known, conventional type, usually formed of metal and comprising male and female fasteners which are, respectively, connected, as by cold forming portions thereof, to the critical zone panel. The male and female fasteners are readily connected, when aligned, by compressive force. These fasteners are readily disconnected by a force in an axial direction, but are highly resistant to separation when forces are exerted in a direction at right angles to their axes.

One advantage incident to the use of snap fasteners of the type illustrated is that they provide means for spacing the upwardly folded edge of the "critical zone" panel from the underlying main portion of that panel, to the end that the trough 32 has an upwardly facing opening. This accentuates a normal tendency of the upwardly projecting edge of the "critical zone" panel to droop or gape to an open position, when the surgical drape is deployed on a patient. All of this goes toward facilitating the ability of the trough to capture liquids incident to a surgical procedure and, further, to capture surgical instruments, that might slip from the "critical zone" panel, thereby preventing the instruments from falling to the floor and becoming a hazard.

While the use of snap fasteners is preferred, the ends of the present invention could be achieved through the use of other fastening means, having similar operating characteristics. By way of illustration, and not as a limitation, hook and loop type fasteners, available under the trade mark Velcro, could be employed.

Other variations from the described embodiment of the invention will occur to those skilled in the art pursuant to the teaching herein, the scope of the invention is, therefore, to be derived from the following claims.

Having thus described the invention, what is claimed as novel and desired to be secured by Letters Patent of the United States is:

1. A reusable, surgical drape adapted to overlie a patient during the performance of a surgical procedure and having a fenestration for registration with the site of a surgical procedure,
    said drape comprising
        a main panel of a given lateral extent,
        a "critical zone" panel of substantially smaller lateral extent and extending outwardly from said fenestration,
    wherein
        the "critical zone" panel comprises
            a liquid proof, barrier panel, and
            a marginal edge portion of the barrier panel is folded on itself to define a bottom, folded portion, said marginal edge portion being in spaced relation to the main portion of the barrier panel and forms an upwardly open, non-filled trough of substantial depth, extending upwardly from the bottom folded portion, for the reception therein of liquids incident to the performance of a surgical procedure, as well as to trap surgical instruments, or the like which might slip from a position on the "critical zone" panel adjacent the fenestration, and
        means are provided for spacing, the edge of the said marginal edge portions from the main portion of the barrier panel, to define a spaced opening for said non-filled trough,
    characterized by
        means for releasably securing said marginal edge portion of the barrier panel to the main portion of the barrier panel, and
    further characterized by means for closing the ends of the trough.

2. A reusable surgical drape as in claim 1 further characterized in that
    the means that close the ends of the trough are releasable to facilitate washing and sterilization of the surgical drape and particularly the "critical zone" panel thereof.

3. A surgical drape as in claim 2 further characterized in that
    the means that close the ends of the trough comprise means for releasably holding portions of the trough forming portions of the "critical zone" panel in further folded relation.

4. A reusable surgical drape as in claim 1 further characterized in that
    the main portion and the folded marginal edge portion of the "critical zone" panel, at opposite ends of the trough, are further folded to close the ends of the trough, and
    releasable means holding said further folded portions in folded relation closing the ends of the trough.

5. A reusable surgical drape as in claim 4 further characterized in that
    each fastening means comprises cooperating male and female snap fasteners,
    a first set of snap fasteners are disposed along the length of the marginal edge portion of the "critical zone" panel and a second set of snap fasteners are disposed in parallel relation to said marginal edge and inwardly therefrom, the two sets of fasteners being generally aligned in a direction at right angles to said marginal edge, whereby the two sets of fasteners may be engaged to releasably maintain the marginal edge portion of the "critical zone" panel in folded, trough-forming relation about a bottom line, and
    the releasable means, holding said further folded portions in folded relation closing the ends of the trough, comprise
    snap fasteners.

6. A reusable surgical drape as in claim 5 further characterized, at each end of the trough, by
    a first male and a first female snap fastener, facing upwardly in the unfolded condition of the "critical zone" panel, and
    a second male and a second female snap fastener, facing downwardly,
    said first male and first female fasteners being engageable to hold the marginal edge portion corner in folded relation on the main portion of the "critical zone" panel,
    the second male and second female fasteners being positioned to face upwardly, when the first male and first female fasteners are engaged,
    said second male and second female fasteners being engageable to hold the folded corner portions of the "critical zone" panel in further folded relation in which the end of the trough is closed.

7. A reusable surgical drape as in claim 6 further characterized in that
    each corner or the "critical zone" panel, at opposite ends of the trough, is curved on a substantial radius to minimize the bulk of material when the portions thereof are folded to form corners for said trough.

8. A reusable surgical drape as in claim 1, further characterized in that the main panel is generally rectangular and has side portions adapted to drape beneath the level of an operating table on which a patient is positioned, the "critical zone" panel is also generally rectangular and has side portions generally parallel with the side portions of the main panel, said "critical zone" panel extends outwardly on opposite sides of the fenestration to a point where both are angled from a horizontal plane, when the surgical draped is draped over a patient, and further characterized in that the marginal edge portion of the opposite side of the barrier panel is folded on itself to define a second, bottom, folded portion, said marginal edge portion of the opposite side being in spaced relation to the main portion of the barrier panel and forming a second upwardly open, non-filled trough of substantial depth for the reception therein of liquids incident to the performance of a surgical procedure, means are provided for spacing the edge of the said marginal edge portions from the main portion of the "critical zone" panel, to define a spaced opening for said second, nonfilled trough, and further characterized by means for releasably securing said marginal edge portion of the "critical zone" panel to the main portion of the "critical zone" panel, and means for releasably closing the ends of the second trough to permit the surgical drape and particularly the "critical zone" panel thereof to be effectively washed and then sterilized, whereby the surgical drape may be washed and sterilized with the "critical zone" panel in an unfolded condition.

9. A reusable, surgical drape adapted to overlie a patient during the performance of a surgical procedure and having a fenestration for registration with the site of a surgical procedure, said drape comprising a main panel of a given lateral extent, a "critical zone" panel of substantially smaller lateral extent and extending outwardly from said fenestration, wherein the "critical zone" panel comprises a liquid proof, barrier panel, and a marginal edge portion of the barrier panel is folded on itself to define a bottom, folded portion, said marginal edge portion being in spaced relation to the main portion of the barrier panel and forms an upwardly open, non-filled trough of substantial depth, extending upwardly from the bottom folded portion, for the reception therein of liquids incident to the performance of a surgical procedure, as well as to trap surgical instruments, or the like which might slip from a position on the "critical zone" panel adjacent the fenestration, characterized by means for releasably securing said marginal edge portion of the barrier panel to the main portion of the barrier panel, and further characterized by means for releasably holding portions of the trough forming portions of the "critical zone" panel in further folded relation which closes the ends of the trough.

10. A reusable surgical drape as in claim 9 further characterized in that the "critical zone" panel overlies the main panel, the fenestration opening is defined by both the main panel and the "critical zone" panel, the fenestration is further defined by a tape edge binding that secures the "critical zone" panel to the main panel, and the "critical zone" panel is further secured to the main panel by stitchings that extend marginally of the ends of the "critical zone" panel, and terminate adjacent the edges of the folded, trough forming portions of the "critical zone" panel.

11. A reusable, surgical drape adapted to overlie a patient during the performance of a surgical procedure and having a fenestration for registration with the site of a surgical procedure, said drape comprising a main panel of a given lateral extent, and having side portions adapted to drape beneath the level of an operating table on which a patient is positioned, a "critical zone" panel of substantially smaller lateral extent, overlying the main panel and extending outwardly from said fenestration, wherein the "critical zone" panel is generally rectangular and has side portions generally parallel with the side portions of the main panel and said "critical zone" panel extends outwardly on opposite sides of the fenestration to a point where the "critical zone" panel and the main panel are both angled downwardly from a horizontal plane, when the surgical drape is draped over a patient, and further wherein the "critical zone" panel comprises a barrier panel, and characterized in that the marginal edge portions of the barrier panel, on opposite sides thereof, outwardly of the fenestration, are folded on themselves to define troughs having bottom, folded portions, the marginal side edges being in spaced relation to the main portion of the barrier panel and forming upwardly open, non-filled troughs of substantial depth, extending upwardly from the bottom folded portions, for the reception therein of liquids incident to the performance of a surgical procedure, as well as to trap surgical instruments, or the like which might slip from a position on the "critical zone" panel adjacent the fenestration, and further characterized by means, capable of being repeatedly attached and detached, for releasably securing said marginal edge portions of the barrier panel to the main portion of the barrier panel, whereby the surgical drape may be washed and sterilized with the barrier panel in an unfolded condition.

12. A reusable surgical drape as in claim 11 further characterized in that the "critical zone" panel overlies the main panel, the fenestration opening is defined by both the main panel and the "critical zone" panel, the fenestration is further defined by a tape edge binding that secures the "critical zone" panel to the main panel, and the "critical zone" panel is further secured to the main panel by stitchings that extend marginally of the ends of the "critical zone" panel, and terminate adjacent the edges of the folded, trough forming portions of the "critical zone" panel.

* * * * *